United States Patent [19]
Imai et al.

[11] Patent Number: 4,843,008
[45] Date of Patent: Jun. 27, 1989

[54] NOVEL MICROORGANISMS AND A NOVEL PROCESS FOR PRODUCING ANTIBIOTICS

[75] Inventors: Harumitsu Imai, Kanagawa; Ken-ichi Suzuki; Shigeru Miyazaki, both of Saitama; Shigenobu Kadota, Tokyo, all of Japan

[73] Assignee: Yamanouchi Pharmaceutical Co., Ltd., Tokyo, Japan

[21] Appl. No.: 810,391

[22] Filed: Dec. 18, 1985

[30] Foreign Application Priority Data

Dec. 24, 1984 [JP] Japan ................. 59-272570

[51] Int. Cl.$^4$ ............... C12N 1/00; C12P 19/62; C12P 17/18
[52] U.S. Cl. .................. 435/252.1; 435/71; 435/119; 435/867
[58] Field of Search ........... 435/76, 169, 253, 867, 435/119

[56] References Cited

U.S. PATENT DOCUMENTS 4,291,021  9/1981  Otani et al. ................ 435/76
4,307,085  12/1981  Waitz et al. ................ 435/76

Primary Examiner—Charles F. Warren
Assistant Examiner—Irene Marx
Attorney, Agent, or Firm—Burgess, Ryan & Wayne

[57] ABSTRACT

Novel microorganisms belonging to the genus *Micromonospora* capable of producing antibiotics YS-02930 K-D, -E or -H represented by formula:

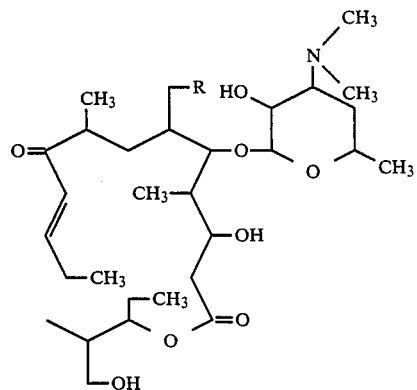

wherein R represents a hydrogen atom or a formyl group and a dotted line represents a double bond or a bond shown by:

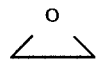

are disclosed. The antibiotics are produced by culturing bacteria belonging to the genus *Micromonospora* capable of producing at least one antibiotic selected from YS-02930 K-D, -E and -H and, harvesting antibiotic YS-02930 K-D, -E or -H.

2 Claims, 4 Drawing Sheets

NOVEL MICROORGANISMS AND A NOVEL PROCESS FOR PRODUCING ANTIBIOTICS

DISCLOSURE OF THE INVENTION

The present invention relates to novel microorganisms belonging to the genus *Micromonospora* capable of producing optional one or two, or all antibiotics selected from YS-02930 K-D, -E and H-substances, and a novel process for producing the antibiotic(s) which comprises culturing said microorganisms and harvesting the antibiotic(s) from the culture solution.

The antibiotics produced in accordance with the present invention are antibiotics of macrolide type shown by the following general formula:

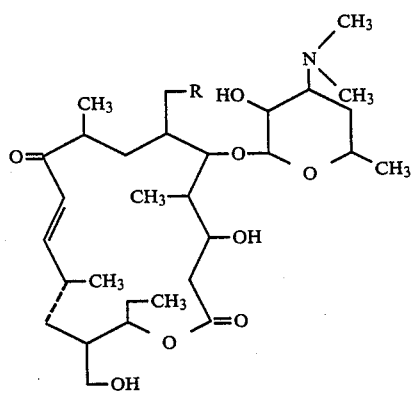

wherein R represents a hydrogen atom or a formyl group and, a dotted line denotes a bond connected by a double bond or

The YS-02930 K-D substance is a compound wherein R denotes a formyl group and the dotted line is a double bond; the YS-02930 K-E substance is a compound wherein R is a formyl group and the dotted line is represented by

and the YS-02930 K-H substance is a compound wherein R is a hydrogen atom and the dotted line is a double bond (hereafter simply referred to D substance, E substance and H substance, respectively).

The D substance is included in the invention disclosed in U.S. Pat. No. 4,438,109 and the E and H substances in U.S. Pat. No. 4,477,443; these substances are all known compounds. According to the former U.S. patent, the D substance is produced by a chemical synthesis process which comprises using as a starting material 3,23-O-methoxymethyl- (or tetrahydrofuranyl)-mycaminosyl tylonolide diethylacetal, deoxygenationing
at the 4'-position thereof and then deblocking protective groups of the hydroxy groups at the 3- and 23-positions and a protective group of the aldehyde group at the 18-position thereof. Further, according to the latter U.S. patent, the E substance is chemically synthesized by a process which comprises treating 4'-deoxymycaminosyl tylonolide diethylacetal with a peracid, then epoxygenationing the 12- and 13-positions and then deblocking the protective group of aldehyde; further the H substance is chemically synthesized by reacting chlorotris(triphenylphosphine)rhodium with 4'-deoxymycaminosyl tylonolide.

However, it has but only been known hitherto to produce the aforesaid antibiotics by a fermentation method, not by the chemical process.

An object of the present invention is to provide novel microorganisms belonging to the genus *Micromonospora* capable of producing these antibiotics. Another object of the present invention is to provide a process for producing the D, E or H substances which comprises culturing microorganisms belonging to the genus *Micromonospora* capable of producing these antibiotics and collecting the D, E or H substances from the culture solution.

As a result of investigating microorganisms capable of producing pharmaceutical substances, the present inventors have found that microorganisms isolated from soil in a conventional manner are found to be novel Actinomycetes belonging to the genus *Micromonospora*, according to their taxonomical characteristics and the Actinomycetes can produce optional one or two, or all antibiotics selected from the D, E and H substances, and have come to accomplish the present invention.

Namely, the present invention is directed to microorganisms belonging to the genus *Micromonospora* characterized by possessing the capability of producing optional one or two, or all antibiotics selected from the D, E and H substances as well as to a process for producing the D, E or H substance characterized by culturing the microorganisms capable of producing the said antibiotic(s) and collecting the D, E or H substance from the culture solution. (Microorganisms)

A specific example of the microorganisms belonging to the genus *Micromonospora* capable of producing optional one or two, or all antibiotics selected from the D, E and H substances includes *Micromonospora* sp. YS-02930 K strain.

Bacteriological properties of the strain YS-02930 K are as follows.

1. Morphological characteristics

No true aerial mycelium is formed on various agar media conventionally used.

Microscopic observation reveal that single (rarely 2) spore(s) is/are formed at the tip of sporophore (0.2 to 0.8 μm) branching from the substrate mycelia and formed all around the whole mycelia.

According to the classification by Luedemann et al. [Antimicrob. Ag. Chemoth., 1964, 47–52 (1965)], the sporophores is formed by Monopodial system.

The spores are spherical (about 0.8–1.2 μm in diameter) and with a smooth surface in electron microscopic observation.

When cultured in liquid medium, hypha is scarcely branched but extended long; and a spherical structure (8 to 10 μm in long diameter) is observed between hyphae. Electron microscopic observation reveals that these structures are formed by fusion of the hyphae.

2. Cultural characteristics on various media

Cultural characteristics on various media are as shown below.

Unless otherwise indicated, the properties are observed in a conventional manner after culturing at 28° C. for 21 days. The color indications are given according to the classifications in Color Harmony Manual (Color Research Laboratories, Japan).

| Medium | | Growth Condition |
|---|---|---|
| Starch (1%) yeast extract (0.2%) agar medium | G | good, dim yellow orange |
| | R | pale yellow brown-dim yellow orange |
| | S | none |
| Glucose-asparagine agar medium | G | good, yellow brown |
| | R | pale yellow brown-yellow brown |
| | S | none |
| Glycerine-asparagine agar medium (ISP-5) | G | no good, brown white |
| | R | colorless-brown |
| | S | none |
| Starch inorganic salts agar medium (ISP-4) | G | somewhat poor, pale yellow brown |
| | R | pale yellow orange-pale yellow brown |
| | S | none |
| Tyrosine agar medium (ISP-7) | G | medium, brown white-yellow brown |
| | R | colorless-brown white |
| | S | none |
| Nutrient agar medium | G | good |
| Yeast maltose agar (ISP-2) | G | good, dim yellow orange-yellow brown |
| | R | dim yellow orange-dark yellow orange |
| | S | none |
| Oatmeal agar medium (ISP-3) | G | good; grayish yellow brown |
| | R | dim yellow orange |
| | S | none |
| Bennett agar medium | G | good, dim yellow orange-yellow brown |
| | R | dim yellow orange-dark yellow orange |
| | S | none |
| Peptone-yeast-iron agar medium (ISP-6) | G | medium, yellow orange |
| | R | yellow orange-dark yellow orange |
| | S | none |

(Notes)
G: color of bacterioflora at the surface of growth and colony
R: color hue of the back surface
S: soluble pigment

3. Physiological characteristics

| (1) | Growth temperature range | 24–40° C. |
|---|---|---|
| | Optimum growth temperature | 30–33° C. |
| (2) | Liquefaction of gelatin gelatin (20° C.) | weakly positive |
| | glucose-peptone-gelatin (28°) | weakly positive |
| (3) | Coagulation of skimmed milk | positive |
| | Peptonization of skimmed milk | positive |
| (4) | Nitrate reduction | negative |
| (5) | Starch hydrolysis | negative |
| (6) | Formation of melanoid pigment tyrosin agar | negative |
| | peptone-yeast-iron agar | negative |

Note: The growth temperature indicates the result of observation from 7 to 21 Days at each temperature (5, 10, 15, 20, 25, 28, 30, 33, 37, 40, 45 and 50° C.). The action on milk indicates the results of the observation at 37° C. from 3 to 21 Days. Others indicate the results of the observation at 28° C. after 2 weeks, unless otherwise indicated.

4. Assimilation of each carbon source
(Pridham-Gottlieb agar medium, cultured at 28° C.)

| Trehalose | − | D-Mannitol | − |
|---|---|---|---|
| D-Fructose | − | D-Galactose | − |
| D-Glucose | ± | Maltose | − |
| L-Arabinose | + | Lactose | − |
| D-Xylose | − | D-Sorbitol | − |
| Sucrose | + | Salicin | − |
| Inositol | − | Glycerine | − |
| L-Ramnose | − | α-Melibiose | ∓ |
| Raffinose | − | Soluble starch | + |

(Notes)
+ : grow
± : slightly grow
∓ : scarcely grow
− : does not grow

5. Analysis of cell wall composition:

According to the Lechevalier et al method (Lechevalier, M. P. et al; pp. 227–228 in Dietz, A. et al ed., Actimonycete Taxonomy, SIM Special publication No. 6, 1980), the cell wall components of the strain and acid hydrolysates of the whole cell were analyzed. As a result, it was confirmed that it contained meso-diaminopimelic acid, 3-hydroxydiaminopimelic acid and glycine as characteristic amino acids and as sugar components, xylose and arabinose.

From the foregoing bacteriological characteristics, the strain YS-02930 K does not form any true mycelium on various agar media but forms a single (rarely 2) spore(s) on sporophore (monopodial type) branching from substrate mycelium. In liquid culture, the hyphae are scarcely branched but extended long. The hyphae are occasionally fused to form spherical structures. By analysis of the cell wall and acid hydrolysates of the whole cell, it was confirmed that it contained meso-diaminopimelic acid and glucine as characteristic amino acid, and as sugars, xylose and arabinose. From the foregoing characteristics, this strain is considered to belong the genus Micoromonospora. In survey of known species of Actinomycetes similar to this strain by Bergey's Manual of Determinative Bacteriology, 8th Edition (1974) and various publications, this strain resembles *Micromonospora chalcea* and *Micromonospora halophytica* in that spores are spherical with smooth surface and the color tone grown on agar media is orange to yellow brown. However, as shown in Table 1, the strain YS-02930 K differs from *M. chalcea* in utilization of carbon sources. *M. chalcea* can utilize α-melibiose, raffinose, L-arabinose, D-glucose, D-fructose, D-galactose, starch, sucrose and D-xylose; whereas the strain YS-02930 K can utilize L-arabinose, D-glucose, sucrose and starch but cannot utilize carbon sources other than those described above (can slightly utilize α-milibiose). Further the strain YS-02930 K has no capability of decomposing cellulose as is noted with *M. chalcea*.

Further, *M. halophytica* can utilize L-arabinose, D-galactose, D-glucose, D-fructose, α-melibiose, raffinose, starch, sucrose and D-xylose as carbon sources, as shown in Table 1 below and, is greatly different from the strain YS-02930 K in utilization of carbon sources. Further, *M. halophytica* differs from the strain YS-02930 K both in reduction of nitrate (positive) and in decomposition of cellulose (positive).

In addition *Micromonospora carbonacea* is similar to the strain YS-02930 K in that spores are spherical with a smooth surface and non-branched long mycelia are formed in liquid culture; and the color tone grown on agar medium is orange~yellow brown~black. However, with respect to utilization of carbon sources, *M. carbonacea* is different from the strain YS-02930 K, as shown in Table 1, in utilization of D-xylose, D-fructose and α-melibiose; and also different in reduction of nitrate. Furthermore, the type of sporophore formation is Sympodial type with *M. carbonacea* but Monopodial type with the stain YS-02930 K.

Table 1. Comparison in Utilization of Carbon Sources (according to the method of PRIDHAM and GOTTLIEB: J. Bacteriol., 56, 107, 1948)

|  | YS-02930K | *M. carbonacea* NRRL 2972 | *M. chalcea* ATCC 12452 | *M. halsphytica* NRRL 3097 |
| --- | --- | --- | --- | --- |
| L-Arabinose | + | + | + | + |
| D-Xylose | − | + | + | + |
| D-Glucose | ± | + | + | + |
| D-Fructose | − | + | + | + |
| Sucrose | + | + | + | + |
| Inositol | − | − | − | − |
| L-Ramnose | − | − | − | − |
| Raffinose | − | − | + | + |
| D-Galactose | − | + | + | − |
| D-Mannitol | − | − | ∓ | − |
| Soluble Starch | + | + | + | + |
| α-Melibiose | ∓ | + | + | + |

+; utilize
±; poorly utilize
∓; scarcely utilize
−; not utilize

In addition, other species belonging to the genus *Micromonospora*, on which the productivity of macrolide antibiotics have been reported, include (1) *Micromonospora rosaria*, (2) *Micromonospora megalomiciae*, (3) *Micromonospora inositola* and (4) *Micoromonospora chalcea* var. *izumensis*; however, (1) produces a soluble pigment of wine red color and shows a characteristic echinulate structure at the surface of spore; (2) grows well on tyrosine agar medium and formation of melanoid is noted; (3) does not grow on glucose asparagine agar and utilizes inositol as only one carbon source; and (4) has better utilization of carbon sources as compared to the strain YS-02930 K, especially, the utilization of α-melibiose and raffinose is noted. From the foregoing points, the above-described 4 species are obviously different from the strain YS-02930 K. From these results, strain YS-02930 K is not identical with the previously described species belonging to the genus *Micromonospora*. Therefore, the strain YS-02930 K is considered to be a novel species of *Micromonospora* and is designated as *Micromonospora* sp. YS-02930 K.

This strain has been deposited in Fermentation Research Institute, Agency of Industrial Science and Technology, Ministry of International Trade and Industry of Japan under the accession number FERM-P No. 7961 (deposited on Nov. 29, 1984). This deposit was changed to an International Deposit under the Budapest Treaty in 1986 and is not identified under Accession number FERM BP-1076.

The microorganiss in accordance with the present invention are also characterized by producing one, two or all substance(s) selected from the D, E and H substances, in addition to the taxonomical characteristics described above. The strains used in the present invention are susceptible to cause variation artificially or spontaneously, as observed in other *Actinomycetes*. The strain YS-02930 K is used to include strains isolated from the natural environment, strains obtained by artificial variation by means of UV rays, X rays, chemicals, etc. and their spontaneous variants.

The microorganisms which belong to the novel species of the present invention are obtained by isolating from natural soil but can easily be accessible by restoring the freeze dried bacteria deposited in the Fermentation Research Institute described above.

Culturing Method

The microorganims in accordance with the present invention are preferably cultured in media comprising nutrient sources which the microorganisms utilize. The media may be any of synthetic, semi-synthetic or natural, solid or liquid media, but liquid media comprising natural nutrient sources are generally preferred. As the nutrient sources added to the media, any carbon sources may be used as long as they are carbonaceous compounds capable of assimilation; examples include arabinose, sucrose, starch, glucose, starch, dextrin, palm oil, soybean oil, α-melibios, etc., which may be used singly or in combination. Further, alcohols, organic acids and the like may also be used in some occasion. As inorganic and organic nitrogen sources, there may be used singly or in combination, ammonium chloride, sodium nitrate, ammonium sulfate, ammonium nitrate, urea, etc.; as organic nitrogen sources, peptone, yeast extract, dry yeast, meat extract, gluten meal, corn steep liquor, soybean powder, fish powder, peanut powder, cotton seed meal, casamino acid or various amino acids (e.g., glutamic acid, alanine, lysine, etc.) and the like.

The media may also be supplemented with sulfates, nitrates, chlorides, carbonates, phosphates, etc. of metals such as sodium, potassium, magnesium, calcium, zinc, iron, cobalt, etc., if necessary.

It is preferred that culture may be carried out under aerobic conditions. The culture may be any of stationary, shake and aerial cultures but shake or aerial culture is advantageous. The culture preferably takes place at a temperature of 25° to 33° C., with particular. preference approximately from 27° to 29° C. Further, the pH of the medium should be maintained around a neutral range from about 5.5 to about 8.5. The incubation period varies depending upon composition of medium, culture conditions such as temperature, etc. but is generally for about 2 to about 14 days. The culture is completed at the right time when the above described antibiotics reach the maximum titer.

The antibiotic(s) is isolated and purified by conventional method. The one or two, or all antibiotics are accumulated in the culture medium when *Micromonospora* sp. YS-02930 K is cultured under the condition described in example.

For isolation and purification of the substances having antibacterial activity, there may be preferably adopted a method by, after centrifuging or filtering the culture solution to remove cells, utilizing difference in dissolution property or solubility in appropriate solvents, difference in precipitation ability or precipitation rate from a solution, difference in adsorption affinity to various adsorbents, difference in distribution between two types of liquid phases, etc. These methods may be used singly, in combination in optional orders or repeatedly, depending upon necessity.

Among the products obtained by culturing the YS-02930 K strain, especially two types of substances (D and E substances) having antibacterial activity are separately spotted on 0.58 and 0.62 of Rf values when a mixture of these substances is chromatographed on Silica Gel 60 $F_{254}$ made by Merck Inc. using chloroform:methanol:28% ammonia water (40:10 : 0.2) as a developing solvent; utilizing this property, these substances may easily be isolated. A purified product isolated from the former spot is the D substance and the E substance is a purified product isolated from the latter spot.

The H substance may be isolated as a spot at 0.62 of an Rf value by thin layer chromatography, on Silica Gel 60 $F_{254}$ thin layer plate made by Merck Inc., using as a developing solvent chloroform:methanol:28% ammonia water (160:40:0.5).

Products

The physicochemical properties of the thus obtained antibiotics are as follows:

(A) Physicochemical Properties of the D Substance (1) Ultraviolet Absorption Spectrum: $\lambda_{max}^{MeOH}$ 283 nm
(2) Infrared Absorption Spectrum: The infrared absorption spectrum of the substance according to the potassium bromide tablet method is shown in FIG. 1.
(3) Nuclear Magnetic Resonance Spectrum: Nuclear magnetic resonance spectrum of the substance in chloroform-d at 100 MHz is shown in FIG. 2.
(4) Mass Spectrum:
Major fragment peaks by EI-MS: 158, 407 and 581 (M+)
Peak of its TMS derivative by EI-MS: 797 (M+)
(5) Appearance: colorless powder
(6) Basic, neutral or acidic: basic substance
(7) Rf values of thin layer chromatography:
Silica Gel 60 $F_{254}$ (made by Merck Inc.) was used: Detection: UV at 254 nm

| Developing Solvents | Rf Value |
| --- | --- |
| Chloroform:methanol (5:1) | 0.22 |
| Chloroform:methanol: 28% ammonia water (40:10:0.2) | 0.58 |

(B) Physicochemical Properties of the E Substance (1) Ultraviolet absorption spectrum $\lambda_{max}^{MeOH}$ 240 nm
(2) Mass Spectrum:
Major fragment peaks by EI-MS: 158, 423 and 597 (M+)
Peak of its TMS derivatives by EI-MS: 813 (M+)
(3) Appearance: colorless powder
(4) Basic, neutral or acidic: basic substance
(5) Solubility: soluble in methanol, ethanol, acetone, ethyl acetate and chloroform
(6) Rf values of thin layer chromatography:
Silica Gel 60 $F_{254}$ (made by Merck Inc.) was used: detection: UV at 254 nm

| Developing Solvents | Rf Value |
| --- | --- |
| Chloroform:methanol (5:1) | 0.25 |
| chloroform:methanol: 28% ammonia water (40:10:0.2) | 0.62 |

(C) Physicochemical Properties of the H Substance:

(1) Ultraviolet absorption spectrum $\lambda_{max}^{MeOH}$ 283 nm
(2) Infrared Absorption Spectrum: The infrared absorption spectrum of this substance by the potassium bromide tablet method is shown in FIG. 3.
(3) Nuclear Magnetic Resonance Spectrum:
The nuclear magnetic resonance spectrum of this substance is chloroform-d at 100 MHz is shown in FIG. 4.
(4) Mass Spectrum:
Major fragment peaks by EI-MS; 158, 174, 379 and 553 (M+)
(5) Molecular Weight and Molecular Formula: 553, $C_{30}H_{51}NO_8$
(6) Appearance: colorless powder
(7) Basic, neutral or acidic: basic substance
(8) Rf values of thin layer chromatography:
Silica Gel 60 $F_{254}$ (made by Merck Inc.) was used: detection: UV at 254 nm

| Developing Solvents | Rf Value |
| --- | --- |
| Chloroform:methanol: 28% ammonia water (160:40:0.5) | 0.62 |

The D, E and H substances described above all exhibit antibacterial activity against pathogenic bacteria such as Gram-positive bacteria, Gram-negative bacteria, Mycoplasma, etc.

From the foregoing physicochemical properties, biological activities, etc., the products of the present invention obtained by fermentation have been identified and the D substance is represented by formula:

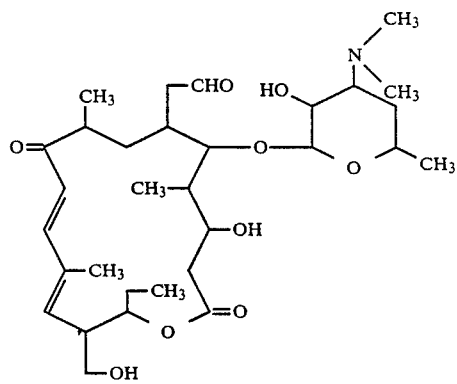

the E substance is represented by formula:

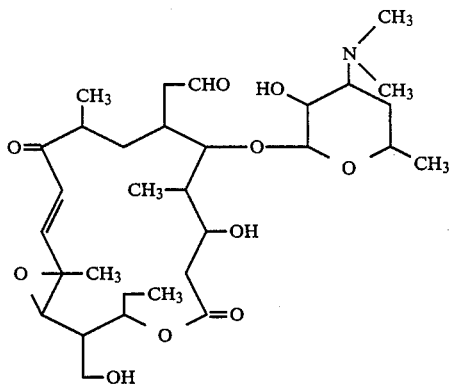

and the H substance is represented by formula:

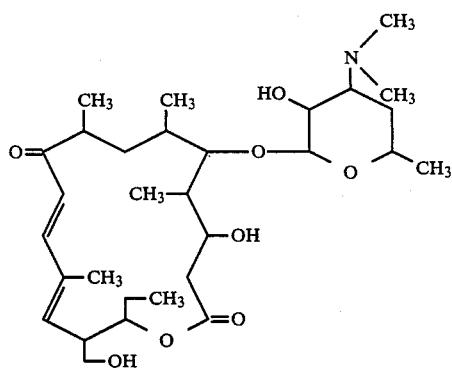

As described above, the each of antibiotics (D, E and H) provided by the process of the present invention exhibits excellent antibacterial activity against pathogenic bacteria such as Gram-positive bacteria, Gram-negative bacteria, Mycoplasma, etc., as compared to conventional macrolide antibiotics, and the antibiotics are useful for prophylaxis and treatment of diseases infected with these bacteria (disclosure of U.S. Pat. No. 4,438,109 is hereby incorporated by reference).

The present invention provides marked effects from an industrial viewpoint in that useful antibiotics (D, E and H) which could have been hitherto produced only by chemical modification of products obtained by fermentation, can be produced directly by the fermentation process.

The present invention will be described in more detail with reference to the examples below.

EXAMPLE 1

Hyphae of *Micromonospora* sp. YS-02930 K strain grown in Bennett's agar medium were scratched off and inoculated in medium (pH 8.0) comprising 2.0% of white dextrin, 0.5% of glucose, 0.5% of polypeptone, 0.5% of yeast extract, 0.52% of brain heart infusion, 0.5% of corn steep liquor, 0.3% of meat extract and 0.2% of calcium carbonate prepared, charged in a 500 ml flask by 60 ml each, and sterilized at 120° C. for 20 minutes. Shaking culture was carried out at 27° C. for 72 hours, which was made a seed culture solution. Next, 3.0% of the seed culture solution was inoculated on 25 liters of medium (pH 7.1) supplemented with 3.0% of potato starch, 1.5% of soybean meal, 0.5% of corn steep liquor, 0.2% of yeast extract, 0.05% of magnesium sulfate heptahydrate, 0.3% of sodium chloride, 0.002% of cobalt chloride hexahydrate and 0.03% of Adekanol (made by Asahi Denka Kogyo K.K.), which had been charged in a stainless-made fermentation tank of a 30 liter volume. Incubation was continued for 72 hours at an aeration rate of 25 liters/min while agitating at 95 to 150 rotations/min at temperatures of 28.0 to 28.5° C., whereby antibacterial activity against *Bacillus subtilis* ATCC 6633 strain became the maximum. Radiolite #600 (Showa Chemical Industry Co., Ltd.) was added to the thus obtained culture solution. After agitating the mixture, it was filtered to obtain 20 liters of the filtrate. After 0.1N sodium hydroxide was added to the filtrate to adjust pH to 8.5, 20 liters of ethyl acetate was added thereto followed by thorough agitation. After the ethyl acetate layer was separated, 5 liters of an aqueous hydrochloric acid solution, the pH of which had been adjusted to 3, were added to the ethyl acetate layer thereto followed by thorough agitation. After separating the aqueous hydrochloric acid layer of pH 3, sodium bicarbonate was added to adjust the pH to 8.5. Then, 5 liters of ethyl acetate were added to the system followed by thorough agitation. The ethyl acetate layer was separated and anhydrous sodium sulfate was added thereto followed by dehydration. Then anhydrous sodium sulfate was separated by filtration. The ethyl acetate layer was then concentrated under reduced pressure to obtain 200 mg of a pale yellow substance.

EXAMPLE 2

After 200 mg of the pale yellow substance obtained in Example 1 was dissolved in a small quantity of methanol, the solution was applied to a thin layer plate of Silica Gel 60 $F_{254}$ manufactured by Merck Inc. in a belt shape, which was chromatographed using as a developing solvent chloroform : methanol:28% ammonia water (40:10:0.2). Fractions shown an Rf value of 0.58 and exhibiting antibacterial activity against *Bacillus subtilis* ATCC 6633 strain were scratched off. The scratched-off silica gel powders were packed in a column to elute a substance having an antibacterial activity with chloroform:methanol:28% ammonia water (40:10:0.2). Thereafter the eluate was concentrated under reduced pressure to obtain 15 mg of pure antibiotic YS-02930 K-D as colorless powders.

EXAMPLE 3

After 200 mg of the pale yellow substance obtained in Example 1 was dissolved in a small quantity of methanol, the solution was applied to a thin layer plate of Silica Gel 60 $F_{254}$ manufactured by Merck Inc. in a belt shape, which was chromatographed using as a developing solvent chloroform : methanol:28% ammonia water (40:10:0.2). Fractions shown an Rf value of 0.62 and exhibiting antibacterial activity against *Bacillus subtilis* ATCC 6633 strain were scratched off. The scratched-off silica gel powders were packed in a column to elute a substance having an antibacterial activity with chloroform:methanol:28% ammonia water (40:10:0.2). Thereafter the eluate was concentrated under reduced pressure to obtain 10 mg of pure antibiotic YS-02930 K-K as colorless powders.

EXAMPLE 4

Hyphae of *Micromonospora* sp. YS-02930 K strain grown in Bennett agar medium were scratched off and inoculated in medium (pH 8.0) comprising 2.0% of white dextrin, 0.5% of glucose, 0.5% of polypeptone, 0.5% of yeast extract, 0.52% of brain heart infusion, 0.5% of corn steep liquor, 0.3% of meat extract and 0.2% of calcium carbonate prepared, charged in a 500 ml flask by 60 ml each, and sterilized at 120° C. for 20 minutes. Shaking culture was carried out at 27° C. for 72 hours, which was made a seed culture solution. Next, 3.0% of the seed culture solution was inoculated on 100 liters of medium (pH 7.1) supplemented with 3.0% of potato starch, 1.5% of soybean meal, 0.5% of corn steep liquor, 0.2% of yeast extract, 0.05% of magnesium sulfate heptahydrate, 0.3% of sodium chloride, 0.002% of cobalt chloride hexahydrate and 0.03% of Adekanol (made by Asahi Denka Kogyo K.K.), which had been charged in a stainless-made fermentation tank of a 150 liter volume. Incubation was continued for 72 hours at an aeration rate of 100 liters/min while agitating at 95 to 150 rotations/min at temperatures of 28.0° to 28.5° C., whereby antibacterial activity against *Bacillus subtilis* ATCC 6633 strain became the maximum. Radiolite #600 (Showa Chemical Industry Co., Ltd.) was added to the thus obtained culture solution. After agitating the mixture, it was filtered to obtain 85 liters of the filtrate. After 0.1N sodium hydroxide was added to the filtrate to adjust pH to 8.5, 85 liters of ethyl acetate was added thereto followed by thorough agitation. After the ethyl acetate layer was separated, 10 liters of an aqueous hydrochloric acid solution, the pH of which had been adjusted to 3, were added to the ethyl acetate layer thereto followed by thorough agitation. After separating the aqueous hydrochloric acid layer of pH 3, sodium bicarbonate was added to adjust the pH to 8.5. Then, 10 liters of ethyl acetate were added to the system followed by thorough agitation. The ethyl acetate layer was separated and anhydrous sodium sulfate was added thereto followed by dehydration. Then anhydrous sodium sulfate was separated by filtration. The ethyl acetate layer was then concentrated under reduced pressure to obtain 800 mg of a pale yellow substance.

EXAMPLE 5

After 800 mg of the pale yellow substance obtained in Example 4 was dissolved in 1 ml of a solution of chloroform : methanol:28% ammonia water (50:1:0.1). Then, 1 ml of the solution was charged a column having packed 16g of Wako Gel C-200 (made by Wako Junyaku K.K.) with chloroform:methanol:28% ammonia water (60:1:0.1), which was chromatographed using as a developing solvent chloroform:methanol:28% ammonia water (50:1:0.1) and fractionated 5 ml each. Each fraction was chromatographed using silica Gel 60 F 254 (made by Merck Inc.) and chloroform : methanol:28% ammonia water (160:40:0.5) as a developing solvent. Fractions shown an Rf value of 0.62 in a detector with UV rays at 254 nm and exhibiting antibacterial activity against *Bacillus subtilis* ATCC 6633 strain were collected. The collected fractions were concentrated under reduced pressure to obtain 20 mg of pure antibiotic YS-02930 K-H as colorless powders.

Figure 1:
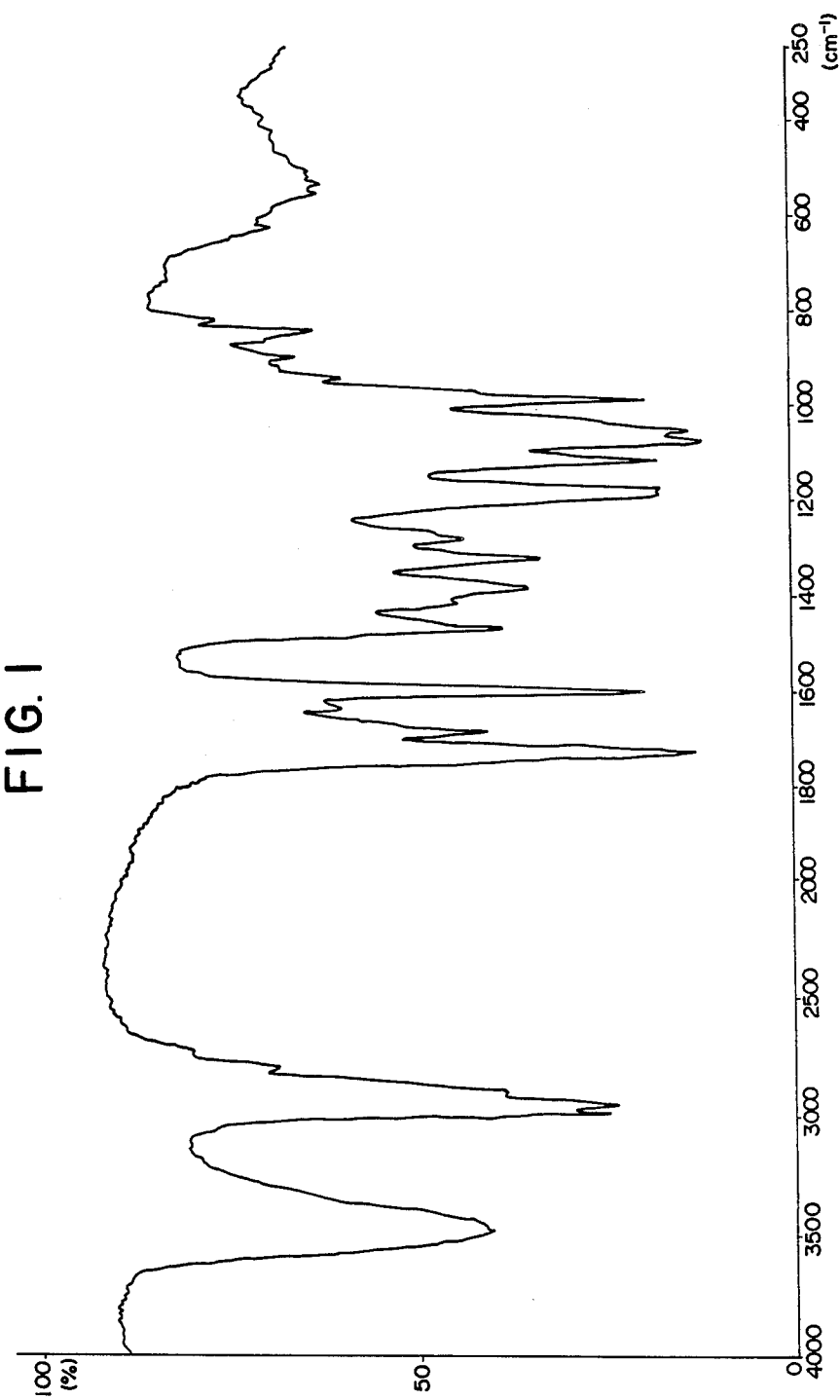
FIG. 1 shows IR spectrum of YS-02930 K-D.
Figure 2:
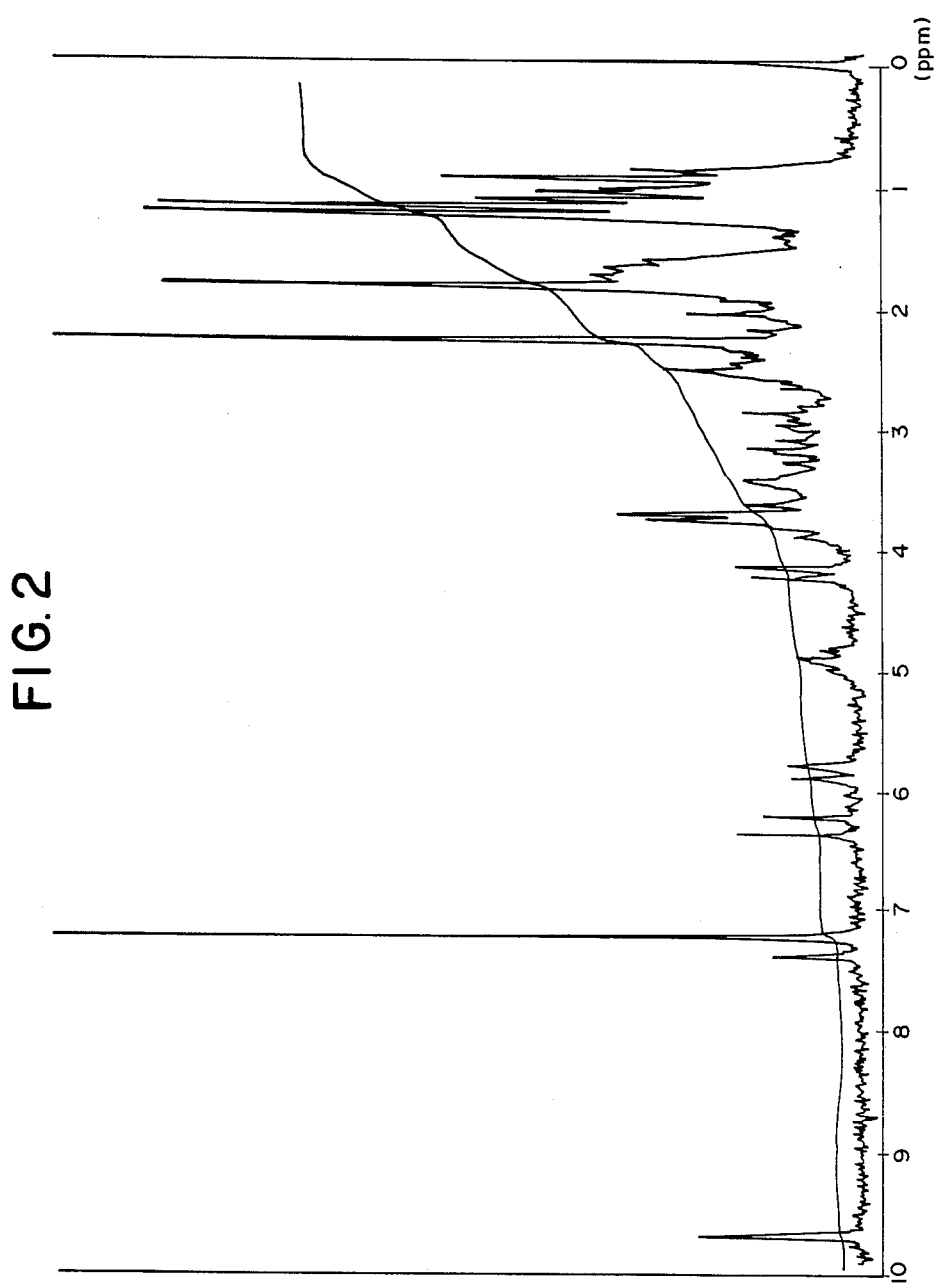
FIG. 2 shows NMR spectrum of the substance.
Figure 3:
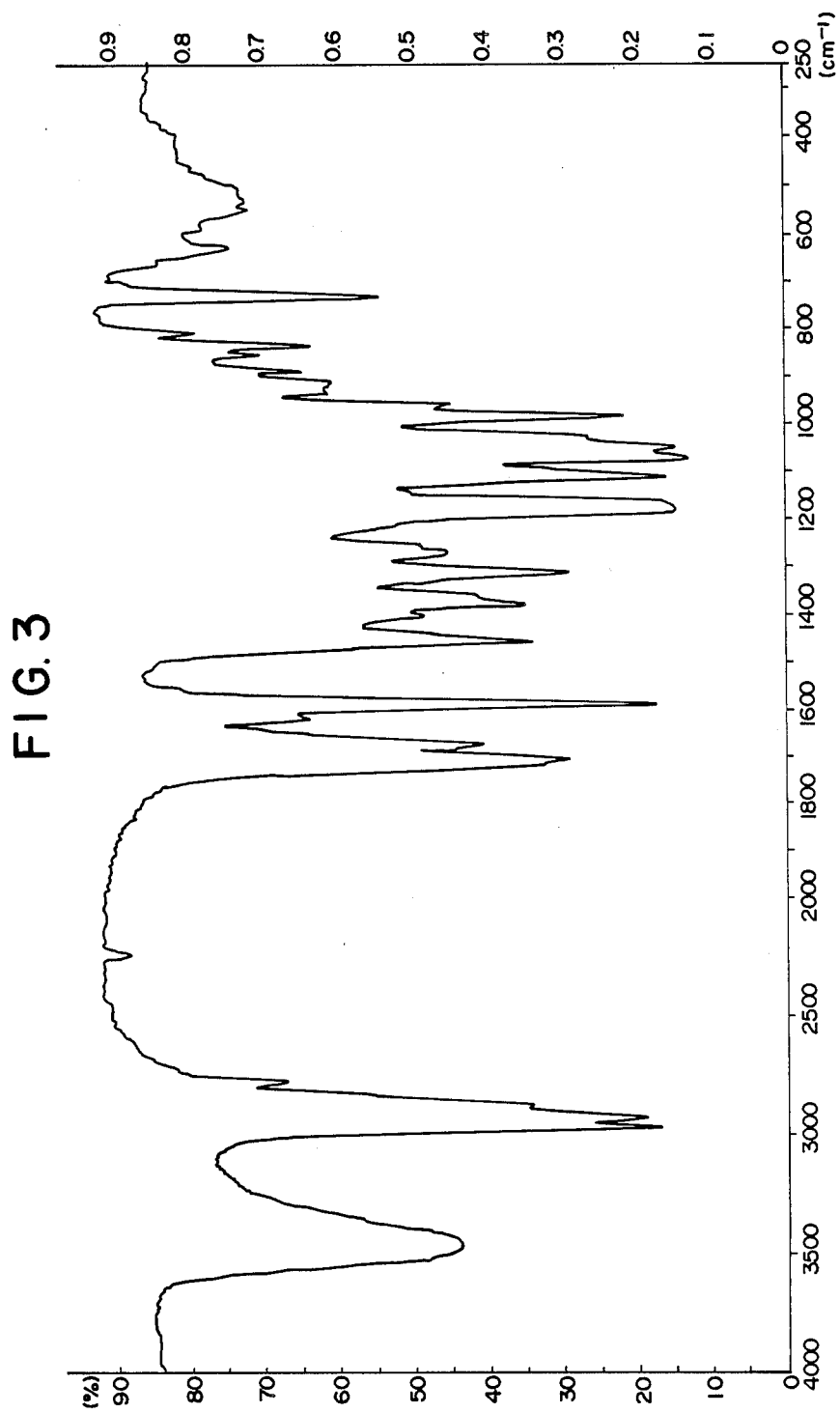
FIG. 3 shows IR spectrum of YS-02930 K-H.
Figure 4:
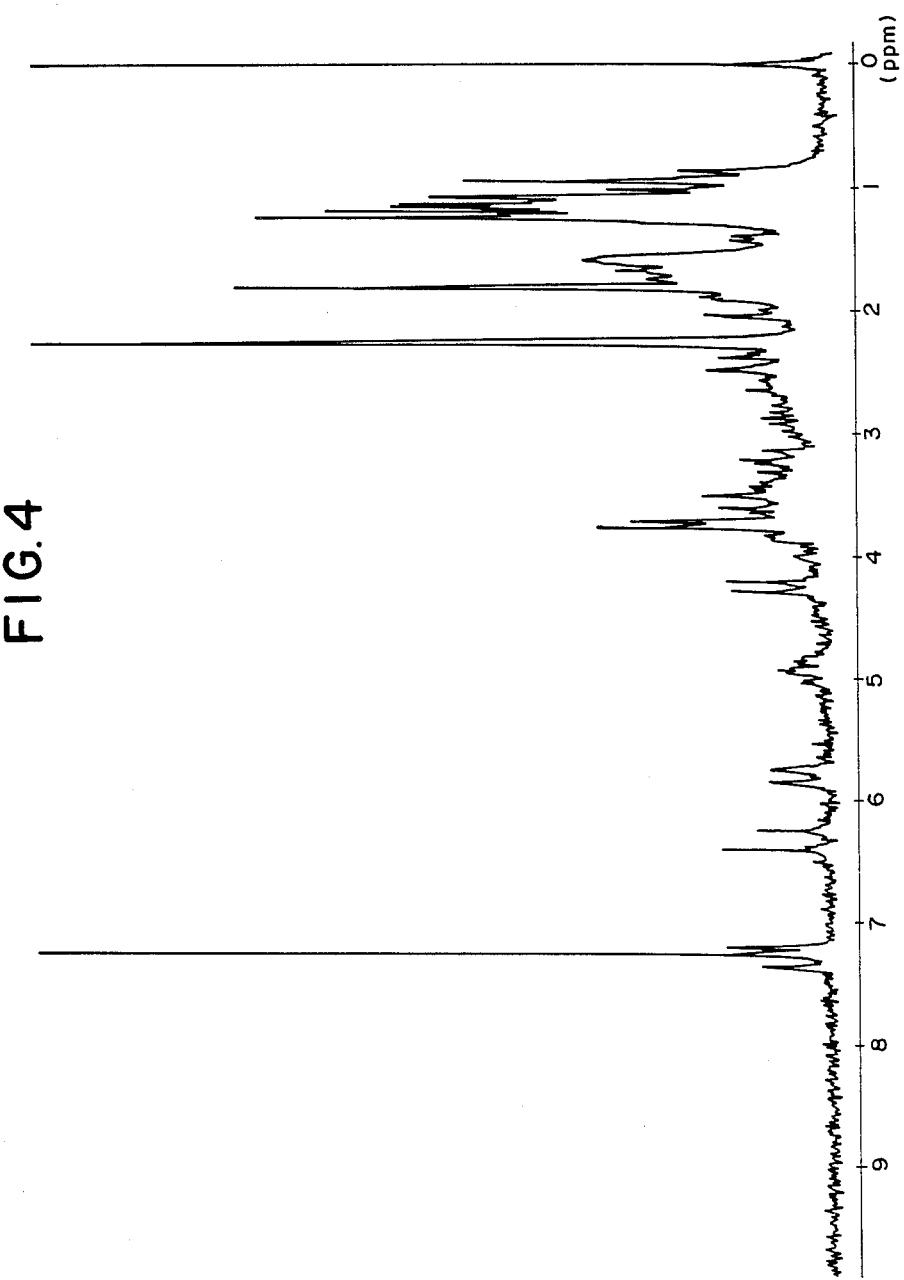
FIG. 4 shows NMR spectrum of the substance.

We claim:

1. A biologically pure culture of *Micromonospora* sp. YS-02930 K strain capable of producing at least one antibiotic selected from the group consisting of YS-02930 K-D, YS-02930 K-E and YS-02930 K-H.

2. A process for producing at least one antibiotic selected from the group consisting of YS-02930 K-D, YS-02930 K-E and YS-02930 K-H which comprises culturing a biologically pure culture of *Micromonospora* sp. YS-02930 K and havesting said antibiotic.

* * * * *